(12) United States Patent
Kuehn et al.

(10) Patent No.: US 9,598,226 B2
(45) Date of Patent: Mar. 21, 2017

(54) DISPENSER

(71) Applicant: STRATEC Biomedical AG, Birkenfeld (DE)

(72) Inventors: Oliver Kuehn, Straubenhardt (DE); Martin Trump, Pforzheim (DE); Michael Burkart, Waldenbronn (DE)

(73) Assignee: STRATEC, Biomedical AG, Birkenfeld, DE (US)

( * ) Notice: Subject to any disclaimer, the term of this patent is extended or adjusted under 35 U.S.C. 154(b) by 0 days.

(21) Appl. No.: 14/627,156

(22) Filed: Feb. 20, 2015

(65) Prior Publication Data
US 2015/0251840 A1 Sep. 10, 2015

(30) Foreign Application Priority Data
Mar. 10, 2014 (GB) .................................. 1404176.8

(51) Int. Cl.
*B65D 83/38* (2006.01)
*G01N 35/10* (2006.01)
*B01L 3/02* (2006.01)
*G01N 35/00* (2006.01)

(52) U.S. Cl.
CPC ............ *B65D 83/38* (2013.01); *B01L 3/0227* (2013.01); *G01N 35/1002* (2013.01); *G01N 35/1016* (2013.01); *B01L 2200/143* (2013.01); *B01L 2300/022* (2013.01); *B01L 2400/0481* (2013.01); *G01N 2035/00801* (2013.01)

(58) Field of Classification Search
CPC ........ B01L 3/0293; B01L 3/0217; B01L 3/52; B01L 3/0231; G01N 35/1002; G01N 35/1016; G01N 2035/1025; G01N 2035/0811; G01N 2035/08211; B65D 83/83; B65D 83/44
See application file for complete search history.

(56) References Cited

U.S. PATENT DOCUMENTS

| | | | | |
|---|---|---|---|---|
| 5,110,558 A | * | 5/1992 | Romer | B01L 3/5082 210/662 |
| 5,525,302 A | * | 6/1996 | Astle | B01L 3/0279 422/511 |
| 5,577,513 A | * | 11/1996 | Van Vlasselaer | B01L 3/5021 600/578 |
| 7,845,499 B2 | * | 12/2010 | Higgins | B01D 21/262 210/360.1 |
| 8,313,954 B2 | * | 11/2012 | Leach | A61M 1/029 210/513 |
| 9,155,495 B2 | * | 10/2015 | Bullington | A61B 5/150389 |
| 2008/0019878 A1 | | 1/2008 | Trump | |

(Continued)

FOREIGN PATENT DOCUMENTS

| EP | 2481480 | 8/2012 |
|---|---|---|
| GB | 2416757 | 2/2006 |

*Primary Examiner* — Brian R Gordon
(74) *Attorney, Agent, or Firm* — 24IP Law Group; Timothy R DeWitt

(57) ABSTRACT

A disposable dispenser unit is disclosed. The disposable dispenser unit comprises a fluid reservoir, a tag for storing information, a dispenser head having a pump chamber and at least one injector nozzle, and a means disposed at the dispenser head for attachment thereof to a diagnostic system, wherein the pump chamber comprises a piston and the piston comprises a volume which can be filled with fluid.

11 Claims, 25 Drawing Sheets

(56) References Cited

U.S. PATENT DOCUMENTS

| | | | |
|---|---|---|---|
| 2013/0078625 A1* | 3/2013 | Holmes | G01N 35/0092 435/6.11 |
| 2013/0092288 A1 | 4/2013 | Schriber | |
| 2015/0140669 A1* | 5/2015 | Boehm | G01F 11/021 436/54 |
| 2015/0238953 A1* | 8/2015 | Grabosch | B01L 3/021 73/864.13 |

* cited by examiner

DISPENSER

BACKGROUND OF THE INVENTION

Field of the Invention

The field of the invention relates to a dispensing device.

Brief Description of the Related Art

This disclosure teaches a liquid handling device, which is used, for example, in a diagnostic system for the dispensing of liquids into an analytical device. Known issues related to current liquid handling devices are a large dead volume of liquid within the liquid dispensing device which results in wasted fluid trapped in the dead volume. The fluid in the liquid dispensing device may also be instable due to the presence of ambient gasses that can lead to degradation of the liquid. There may also be an issue associated with confusion by the operator between the bottles and the tubing lines on prior art devices. There are also issues related to collection of debris on injector nozzles in the prior art devices, which can accumulate over time and lead to false results or result in malfunction.

Current diagnostic systems have a liquid handling device, which comprises a bottle containing consumable fluids, an aspiration line connected to an outlet of the bottle, and a dispensing pump with a dispense line connected to an injection nozzle. The bottle is the sole consumable part in the liquid handling device. All of the other components are integrated within the diagnostic system and can only be replaced with some difficulty.

One example of a prior art device is known from US patent application publication No. US 2013/0092288 (Schriber, assigned to Tecan Trading). This patent application teaches a dispenser for delivering flowable or pourable material from a container to an outlet end of the line. The liquid handling device shown in this patent application has a long tube with large dead volumes between the bottle and the injection nozzle, which as noted above comprises wasted fluid volume with associated costs of the wasted fluid.

A further example of a liquid handling device used in the art is a pipetting system. Such pipetting systems are known, for example, from United States patent application publication No. US 2008/0019878 (Trump, assigned to Stratec Biomedical Systems AG). This US patent application teaches a positioning device provided for positioning pipettes in a diagnostic device.

The European Patent Application EP 2 481 480 A1 discloses an apparatus including a fluid reservoir and a compressible metering chamber including a first end coupled to the fluid reservoir and a second end. The apparatus further includes a valve coupled to the second end of the metering chamber and a nozzle coupled to the valve. A compressive force is applied to the metering chamber to eject a predetermined amount of fluid. When the compressive force is removed, the metering chamber is refilled.

The UK Patent Application GB 2 416 757 A discloses an apparatus for dispensing a flowable foodstuff. The apparatus comprises a reservoir. Two non-return valves lead into and out of a chamber, and a pump piston is moveable within the chamber to vary the size of the chamber. The piston does not comprise a volume which can be filled with fluid because the piston together with the piston shaft simply adjust the volume of the chamber which is in turn filled with fluid. This apparatus also has a long tube with large dead volumes between the reservoir and the injection nozzle, which as noted above comprises wasted fluid volume with associated costs of the wasted fluid.

Many of the chemicals dispensed in the fluid may be sensitive to air, or other gases, and so the stability of the fluid may be limited if an open bottle or other container is used. On the other hand, an open bottle is often used in order to avoid the need to reduce the pressure above the fluid during removal of the fluid out of the bottle. Such liquid dispenser devices may further require additional air-inlet filters to filter any incoming gases and to avoid degeneration of the fluid in the bottle. These air-inlet filters add to the costs of the diagnostic devices.

The use of the consumable bottles, in particular those with the same shape for different fluids, brings a further problem of the correct placement of the individual aspiration line to the correct bottle. Even in those cases in which the user identifies the bottle and the correct aspiration line, experience has shown that mistakes may occur which lead either to incorrect results or contamination of the liquid handling device. The contamination of the system may require intensive cleaning to enable the system to be reused.

SUMMARY OF THE INVENTION

It is an object of the invention to provide a disposable dispenser unit, which is easy and cheap to replace as part of a liquid handling device. It is a further object of the invention to provide a liquid handling device, during operation of which production of waste and degeneration of handled liquids are reduced.

A disposable dispenser unit is disclosed. The disposable dispenser unit comprises a fluid reservoir, a tag for storing information, a dispenser head having a pump chamber and at least one injector nozzle, and a means disposed at the dispenser head for attachment of the disposable dispenser to a diagnostic system, wherein the pump chamber comprises a piston and the piston comprises a volume which can be filled with fluid.

The tag may be an RFID tag and the diagnostic system comprises an RFID reader.

The disposable dispenser unit may be made of an opaque material.

The pump chamber may further comprise an inlet valve and/or an outlet valve.

In one aspect, the pump chamber comprises an inlet valve and an outlet valve and the piston comprises the inlet valve.

In another aspect, the pump chamber comprises an inlet valve and an outlet valve and the piston comprises the outlet valve.

The disposable dispenser unit may further comprise a fluid sensor for detecting a fluid within the fluid reservoir.

The fluid reservoir may be a bag or a bottle.

The bag may be flexible.

The bag may be located within a container.

The fluid reservoir may be located above the pump chamber.

The fluid reservoir may be directly connected to the pump chamber, and/or the pump chamber may be directly connected to the at least one injector nozzle.

The disposable dispenser unit may further comprise a measurement chamber.

A liquid handling device is disclosed. The liquid handling device comprises a disposable dispenser unit comprising a fluid reservoir, a tag for storing information, a dispenser head having a pump chamber and an injector nozzle, and means disposed at the injector nozzle for attachment of the disposable dispenser to a diagnostic system, wherein the pump chamber comprises a piston and the piston comprises a volume which can be filled with fluid.

The liquid handling device may further comprise a disposable dispenser cartridge actuator.

The disposable dispenser cartridge actuator may comprise a fluid detection sensor.

A use of a disposable dispenser unit for handling liquids is disclosed, the disposable dispenser comprising a fluid reservoir, a tag for storing information, a dispenser head having a pump chamber and an injector nozzle, and means disposed at the injector nozzle for attachment of the disposable dispenser to a diagnostic system, wherein the pump chamber comprises a piston and the piston comprises a volume which can be filled with fluid.

DETAILED DESCRIPTION OF THE INVENTION

Figure 1:
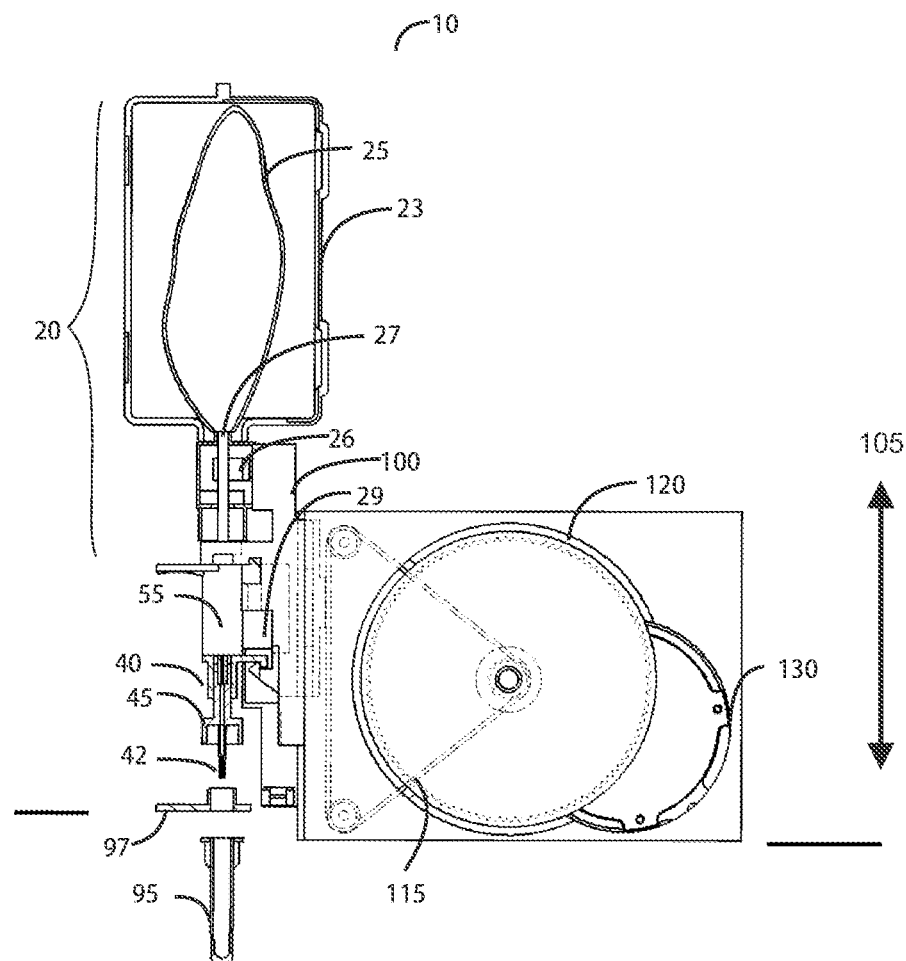
FIG. 1 shows an overview of the liquid handling device of a first aspect.

A disposable dispenser is disclosed which comprises a fluid reservoir, a pump chamber and at least one injection nozzle. The disposable dispenser may be part of a liquid handling device. The liquid handling device may be a diagnostic system or a part of a diagnostic system for analysing fluids for diagnostic purposes. The disposable dispenser unit may also be termed a disposable dispenser cartridge (DDC).

The terms fluid and liquid are used synonymously throughout the present application.

The fluid reservoir may be located above of, and is fluidly connected to, the pump chamber. The fluid reservoir may be located elsewhere than above, e.g. sideways, of the pump chamber. The pump chamber may be located above of, and is fluidly connected to, the injector nozzle. The pump chamber may be located elsewhere than above, e.g. sideways, of the injector nozzle. The fluid reservoir is fluidly connected to the pump chamber through a direct fluid connection, i.e. by fluidly connecting an outlet of the fluid reservoir, e.g. an opening of the fluid reservoir, to an inlet of the pump chamber, e.g. an inlet valve of the pump chamber such that no further connection means are required. In case the fluid reservoir is a bottle, the direct connection may also be a one-way, snap-on connection. Fluid reservoir and pump chamber may then be easily connected after filling the reservoir. The fluid reservoir may also be fluidly connected to the pump chamber by means of a tube or the like. The fluid connection may be, but is not limited to, an opening, a valve, or a tube. The location of the fluid reservoir above the pump chamber enables fluid from the fluid reservoir to be pumped and/or run through the direct fluid connection into the pump chamber. In case of the direct fluid connection, the liquid handling device has a very small dead volume and thus little fluid is wasted. Costs are therefore reduced, especially for expensive diagnostic fluids. The location of the fluid reservoir above the pump chamber furthermore reduces the risk of air entering the pump chamber. Furthermore, fluid from the fluid reservoir is thereby readily available to the pump chamber. The fixed connection between the fluid reservoir and the dispenser head ensures that there is no misconnection. The risk of wrong results of the diagnostic system is reduced.

The pump chamber houses a space, a volume of which can be increased or decreased. Increasing the volume of the space housed by the pump chamber produces a vacuum within the space, leading to inflow of fluid via a fluid connection. Decreasing the volume of the space housed by the pump chamber produces an excess pressure within the space, leading to outflow of fluid via an outlet of the pump chamber towards, for example, a dispensing position such as an opening of a tip. The increasing or decreasing of the volume of the space of the pump chamber results from a force acting on a bounding surface of the space of the pump chamber. The force may result from the injector nozzle abutting on an actuator. The pump chamber may comprise, among others, a piston, a plunger, or bellows. The pump chamber may be made of a rigid material, such as in case of pump chambers with pistons or plungers, or may be, partially or completely, made of a flexible material, such as in case of bellows or of the tubing of a peristaltic pump.

The pump chamber and the injector nozzle, when fluidly connected to one another, form a dispenser head, the dispenser head being fluidly connectable to the fluid reservoir via the inlet of the pump chamber. Fluid provided within the fluid reservoir can thus be dispensed by means of the dispenser head. The fluid connection between the pump chamber and the injector nozzle is a direct fluid connection. The pump chamber and the injector nozzle may also be fluidly connected by means of a tube or the like.

The dispenser head may further comprise a biasing element. The biasing element biases the pump chamber from an actuated state towards a non-actuated state. The volume of the pump chamber is larger in the non-actuated state than in the actuated state. The difference of the volume in the non-actuated state and in the actuated state is predetermined. The biasing element may be, but is not limited to, a compression spring or a torsion spring.

The design of the dispenser head defines the dispense volume. The dispense volume repeatability is improved.

The pump chamber comprises a piston and the piston comprises a volume which can be filled with fluid. That means that the piston itself is hollow and has at least two openings, wherein at least one of the openings may comprise a valve, so that the fluid that is to be dispensed flows through the piston to the injector nozzle. In other words, the fluid which passes through the pump chamber also passes through the piston itself and not only enters a chamber adjacent to the piston. The piston thereby moves relative to the housing of the pump chamber. The valve may be an inlet valve or an outlet valve. The piston can therefore be assembled within the pump chamber which reduces the space needed. A separate piston which does not comprise a volume which can be filled with fluid needs more space within the diagnostic system. The piston may work against hard stops within the pump chamber determining the pump volume.

The fluid reservoir, the pump chamber, and the injector nozzle are disposable and can be disposed of either simultaneously or independently. The fluid reservoir and the dispenser head, when fluidly connected to one another via the pump chamber, form a disposable dispenser unit. The disposable dispenser unit thus comprises the fluid reservoir, the pump chamber, and the injector nozzle.

The disposable dispenser unit is moveable as a unit. Thereby the injector nozzle of disposable dispenser unit may be moved towards a dispensing location.

In one aspect of the disclosure, the fluid reservoir comprises a bag. The bag is flexible and is made of a flexible material. The bag may or may not be located within a container. The container may be made of cardboard, plastic or metal. The container may also be a hardcover bottle. The hardcover bottle might consist of polyethylene (PE). The hardcover bottle allows a comfortable handling of the liquid reservoir during filling and when otherwise handling of the reservoir. There are venting holes in the bottom of the hardcover bottle. When the bag is emptied completely, the bag collapses and remains flat in the middle of the hardcover bottle. The bag is sealed from the surroundings, and removal of fluid from the bag into the pump chamber leads to a collapse of the bag due to atmospheric pressure. Use of a bag eliminates the risk of the fluid within the bag being contaminated by the ambient gases during aeration, or undergoing any change due to contact with the ambient gases. Chemical stability of the fluid is thus ensured or increased. In addition, the "on board stability" is thereby increased and so is the processing security. The overall fluid volume can also be increased, allowing a much longer range of usage within the diagnostic system. Usage of a bag alone or within a container, in addition to locating the fluid reservoir above the pump chamber, further reduces the risk of air entering the pump chamber. During deflating of the bag, the pressure within the bag is more or less constant (except hydrostatic pressures) avoiding unintended dispensing.

An RFID tag, storing information pertaining to the identity of the fluid, e.g. a chemical composition, an origin, or a date of manufacture of the fluid, may be connected to the disposable dispenser unit in order to identify the fluid within the fluid reservoir and thus ensure that the correct fluid reservoir is attached to the pump chamber. This, in conjunction with an RFID reader, ensures that there is no misconnection of the fluid reservoir to the pump chamber.

The disposable dispenser unit can be replaced easily and efficiently and this removes substantially the risk of debris accumulating on the pump chamber and/or injector nozzle. Dispense reliability is improved.

The measurement chamber helps to determine whether the fluid reservoir is fluid-filled. A fluid detection sensor may connect to the measurement chamber to detect whether the measurement chamber is fluid-filled or air-filled. The measurement chamber may be comprised in the disposable dispenser unit. In one embodiment, the measurement chamber is comprised in the fluid reservoir. In another embodiment, the measurement chamber is comprised in the dispenser head.

In one embodiment, the liquid handling device comprises a bag in a bottle as the fluid reservoir, a direct fluid connection between the fluid reservoir and the dispenser head, the disposable dispenser unit is made of an opaque material, and a fluid detection sensor. The bag in a bottle has the advantage that no valve is necessary because air cannot be aspirated. The direct fluid connection avoids a tube at the outlet and thus ensures minimised dead volume. The piston in this embodiment is working against hard stops determining the pump volume. The piston is hollow. The opaque material allows protection of the fluid from light.

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

FIG. 1 shows a first aspect of a liquid handling device 10. The liquid handling device 10 comprises a fluid reservoir 20, comprising a bag 25 and a container 23, and fluidly connected at an opening 27 to a pump chamber 55, the pump chamber 55 being fluidly connected to an injector nozzle 40 with a tip 42. The pump chamber 55 and the injector nozzle 40, when fluidly connected, form the dispenser head 230. The dispenser head 230 is fluidly connectable to the fluid reservoir 20 via the pump chamber 55. The dispenser head 230 and the fluid reservoir 20, when fluidly connected, form the disposable dispenser unit 20, 55, 40. The disposable dispenser unit comprises the fluid reservoir 20, the pump chamber 55, and the injector nozzle 40.

A protective cap 45 is disposed at and surrounds the tip 42 of the injector nozzle 40. The protective cap 45 protects a fluid 22 (shown in FIG. 7) within the injector nozzle from exposure to light. The protective cap 45 furthermore forms an abutment part 45 of the liquid handling device 10, as explained below. Between the opening 27 and the injector nozzle 40, the pump chamber 55 and an inlet valve 62 as well as an outlet valve 64 are disposed, as will be illustrated in more detail in FIG. 4. The pump chamber 55 has a known volume and can be used to dispense a known volume of the fluid 22.

The fluid 22 is contained in the fluid reservoir 20, which is mounted above the injector nozzle 40. The fluid 22 runs from the fluid reservoir 20 into the pump chamber upon opening of one or more of the inlet valve 62 and the outlet valve 64. Neither the fluid reservoir 20 the pump chamber nor the injector nozzle 40 are open to the ambient environment. The tip 42 has a tip opening through which the fluid 22 can be pumped out, when one or more of the inlet valve 62 and the outlet valve 64 are opened, but is otherwise sealed from the environment.

It will be noted that a tag 29, such as an RFID tag, can be attached to the fluid reservoir 20 or the dispenser head 230, e.g. the pump chamber 55, to enable the fluid 22 in the fluid reservoir 20 to be identified. The tag 29 can be programmed and read out, as known in the art, the tag comprising a memory. The memory stores information pertaining to the identity of the fluid 22, such as, but not limited to, a chemical composition, an origin or a date of manufacture. Furthermore, the tag 29 may be a read-write tag. The tag 29 could be replaced by another form of identifier, such as but not limited to a barcode, a QR code or machine-readable alphanumeric code and can be located elsewhere on the disposable dispenser unit. Furthermore, a fluid sensor 26 is disposed at the reservoir 20 in proximity to the opening 27. The fluid sensor 26 senses the presence or absence of the fluid 22 within the reservoir 20, for instance within the lower part of the reservoir 20. The fluid sensor 26 can thereby monitor consumption of fluid 22 in the fluid reservoir 20. Information pertaining to the consumption of fluid 22 may be stored on the read-write tag.

The liquid handling device 10 further comprises an identification reader-writer, such as an RFID reader-writer, for writing information onto and reading information from the read-write tag.

An RFID tag attached to the dispenser head can thus be used to positively identify the attached fluid reservoir at the dispense location. In combination with a read-write RFID tag, also the remaining fill volume (inventory) of the fluid reservoir can be monitored.

The disposable dispenser unit is attached to a carriage 100 or the liquid handling device 10. The carriage 100 is disposed at the dispenser head 230 and is a means for attaching the disposable dispenser to a diagnostic system. The carriage 100 can be moved as a unit up or down in a vertical manner or vertical direction (z-direction), as shown by the double headed arrow 105. A drive 115, 120, 130 comprising a stationary cogwheel 120 attached to a stationary motor 130 is used to move the carriage 100 by moving a belt 115 connected to the carriage 100.

The fluid reservoir 20 may be made of glass or plastic. The fluid reservoir 20 may further incorporate a light resistant layer to reduce the risk of degeneration of the fluid 22 in the fluid reservoir 20, for example under the influence of UV light or other ambient light. The light resistant layer could be a layer of black plastic or be a UV filter. Furthermore, the disposable dispenser unit (20, 55, 40) may be made of an opaque material, such as a black plastic material, for protection of the fluid 22 from light.

Figure 2:
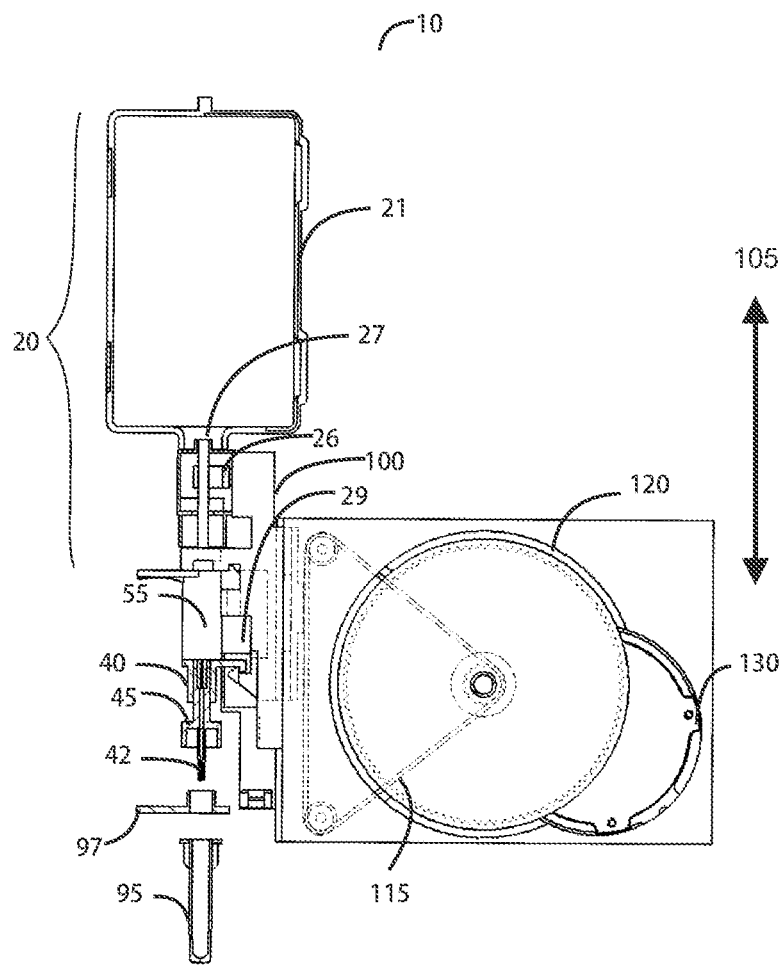
FIG. 2 shows an overview of the liquid handling device of a second aspect.

FIG. 2 shows a second aspect of this disclosure. The same reference numbers are used in FIG. 2 as are used in FIG. 1. In this second aspect, the fluid reservoir 20 comprises a bottle 21. The bottle 21 includes an inlet filter or compensation valve to enable pressure compensation with in the bottle 21 during removal of the fluid 22. A flexible element could also be included in or on the bottle 21 to compensate for pressure changes.

Figure 3:
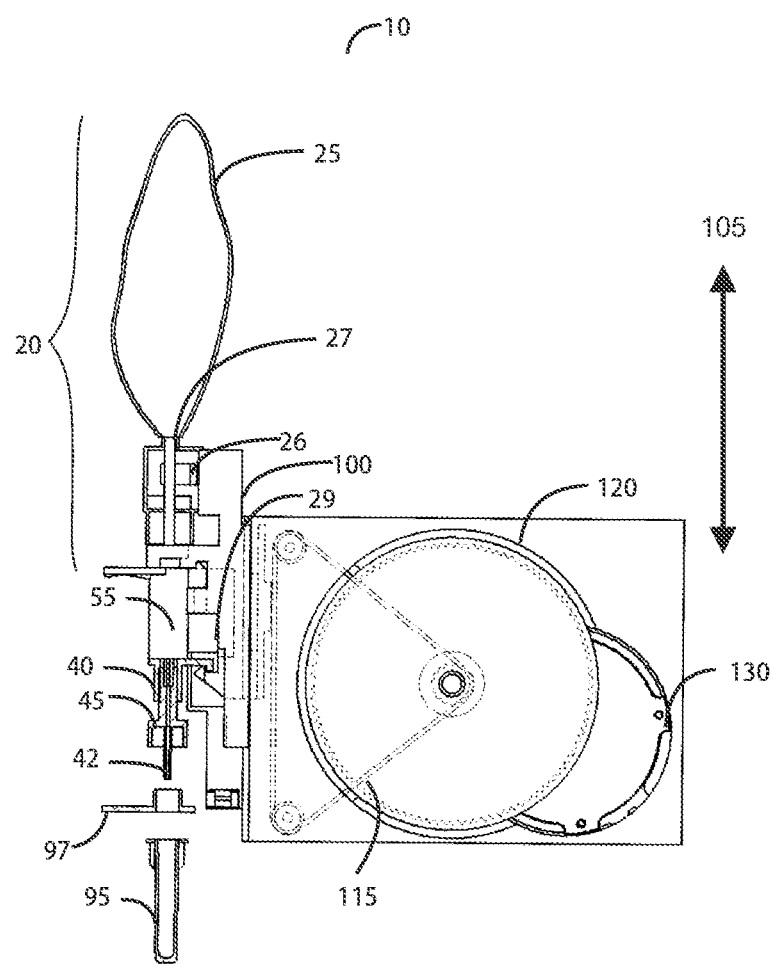
FIG. 3 shows an overview of the liquid handling device of a third aspect.

FIG. 3 shows a third aspect of the invention in which the fluid reservoir 20 comprises a bag 25 that is not contained within a container 23. The opening 27 of the bag 25 may be connected to the pump chamber 55 by means of a connecting tube (not shown). A connecting tube is useful in situations, in which the fluid reservoir 20 cannot be arranged above the dispenser head. The other elements of the liquid handling device 10 remain otherwise unchanged.

Figure 4:
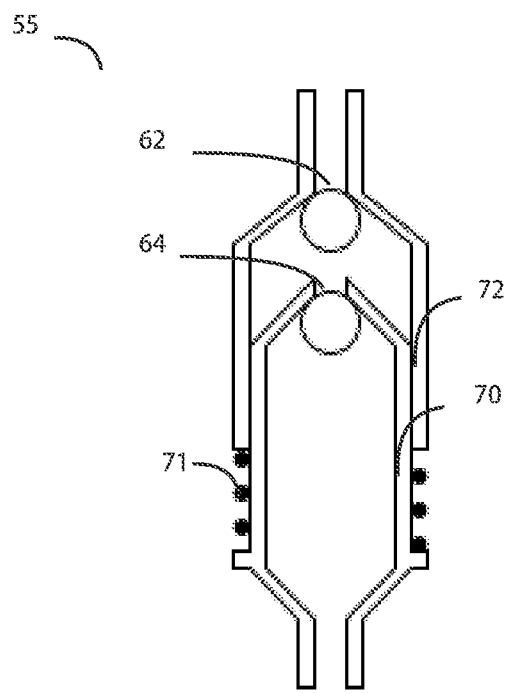
FIG. 4 shows an aspect of a section of a pump chamber between the fluid reservoir and the injector nozzle

FIG. 4 shows an aspect of the pump chamber 55 in more detail. In this aspect, the pump chamber 55 comprises a piston 70, a housing 72, the inlet valve 62, the outlet valve 64, and a spring 71. The piston 70 comprises the outlet valve 64. In this aspect, the inlet valve 62 and the outlet valve 64 are ball check valves, wherein a ball or otherwise shaped body blocks a flow of a fluid by contacting a more or less conical surface. The inlet valve 62 and the outlet valve 64 may also be ball spring valves, duckbill valves, diaphragm check valves, but are not limited thereto. The piston 70 is moveable with respect to the housing 72. The spring 71 constitutes a biasing element and biases the piston 70 towards a non-actuated position with respect to the housing 72. The pump chamber 55 thereby is in a non-actuated state.

The fluid 22 from the fluid reservoir 20 enters the pump chamber 55 through the opening 27 into the pump chamber 55, when the inlet valve 62 is open. The fluid 22 fills a space of the pump chamber 55 of known volume. Thus the amount of fluid 22 dispensed is accurately repeated.

When the piston moves against the force of the spring 71 away from the non-actuated position (upwards in FIG. 4), the outlet valve 64 is opened and the inlet valve 62 is closed. The fluid 22 thus enters the piston 70 from the pump chamber 55. The fluid 22 entering the piston 70 may move fluid 22 present in the injection nozzle 40. Thereby, fluid 22 of a known volume is dispensed through the tip opening of the tip 42.

The pump mechanism may also be of a different type, such as, but not limited to, the mechanism used in a membrane, a piston, a bellows, or a peristaltic pump.

Figure 5A:
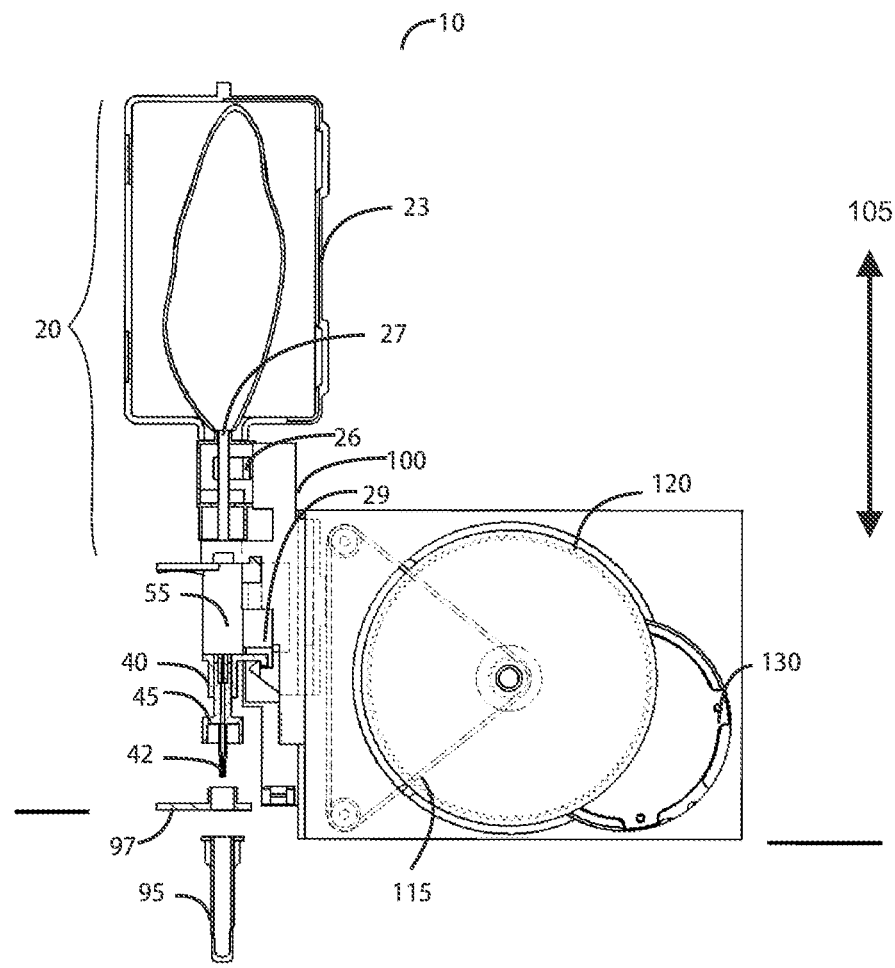
FIGS. 5A to 5C show the operation of the liquid handling device.
Figure 5B:
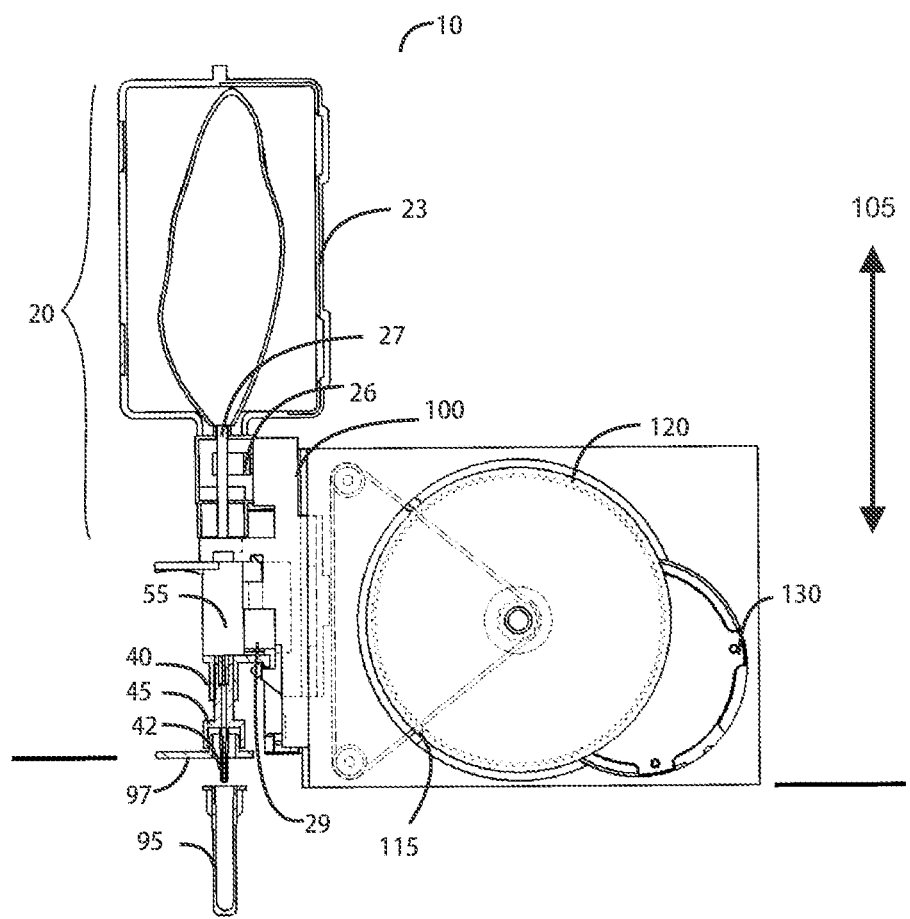
Figure 5C:
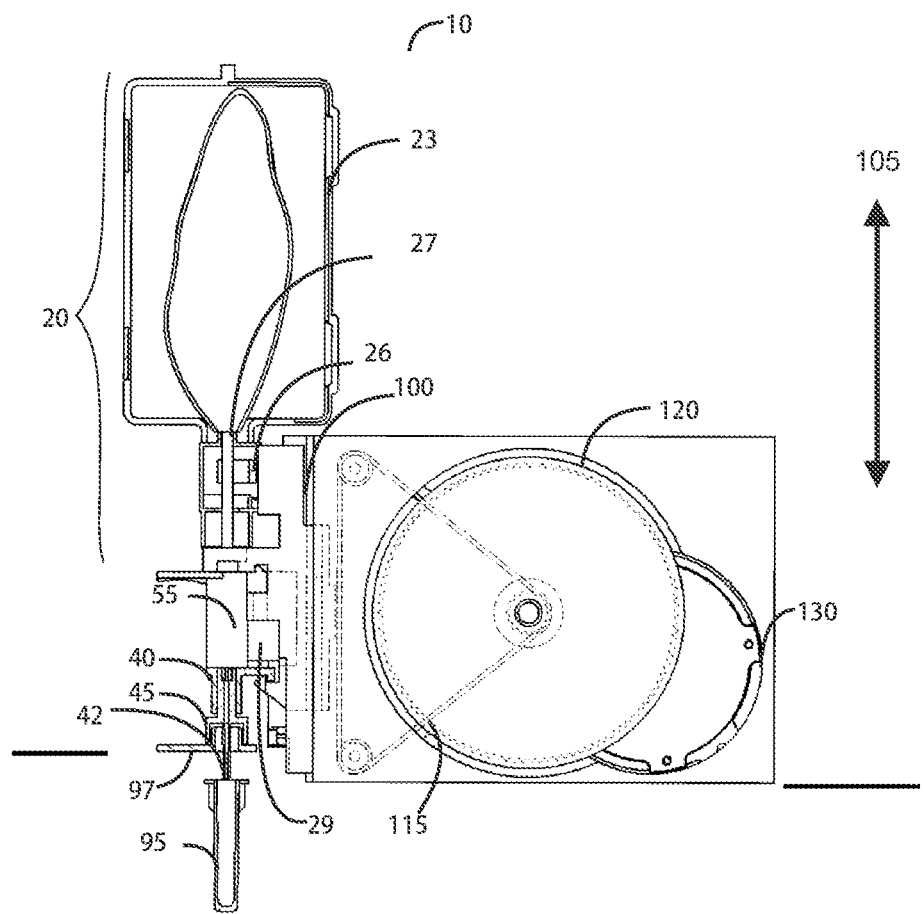

FIGS. 5A-5C show an operating sequence of the liquid handling device. In FIG. 5A, the liquid handling device 10 is located above the vessel 95 into which the fluid 22 is to be added. An actuator 97 is located above the vessel 95. The vessel 95 may be a bottle or a well of a multi-well plate and can be part of an analytic device.

The fluid reservoir 20, the pump chamber 55, and the injector nozzle 40 are moved as a unit by moving the carriage 100 vertically (in the z-direction), as indicated by the double headed arrow (105), such that the tip 42 of the injector nozzle 40 passes through a bore of the actuator 97.

Figure 6:
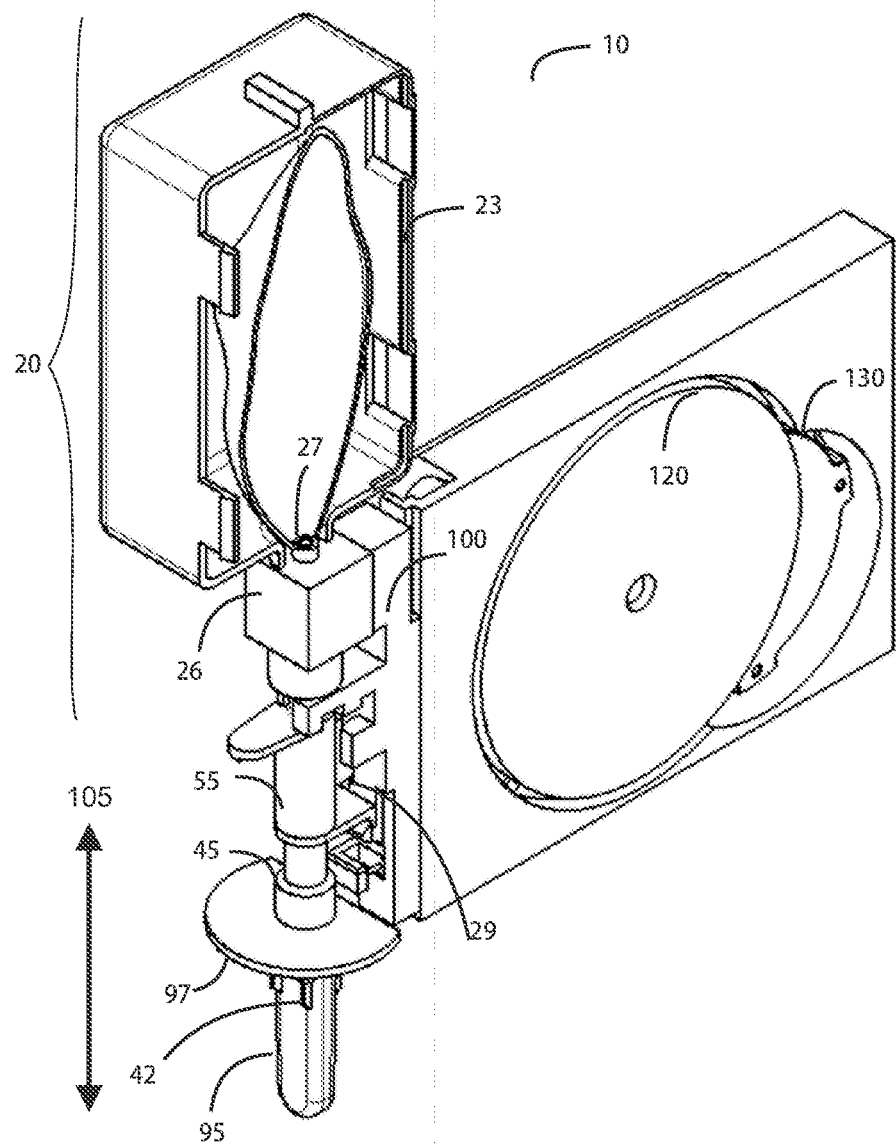
FIG. 6 is a perspective view of the liquid handling device, as shown in FIG. 1, in a condition corresponding to the condition of FIG. 5B.

FIG. 5B shows the inside of the protective cap 45 abuts the top surface of the actuator 97 upon moving the fluid reservoir 20, the pump chamber 55, and the injector nozzle 40 as a unit by a predetermined distance towards the actuator 97. The protective cap thus constitutes the abutment part 45. FIG. 6 shows from a perspective the liquid handling device 10 in the same condition as in FIG. 5B.

As shown in FIG. 5C, moving the injector nozzle 40 further causes, in case of the aspect of the pump chamber 55 as shown in FIG. 4, the piston 70 to move with respect to the pump chamber 55, so as to close the inlet valve 62 and open the outlet valve 64. Thereby, liquid in the pump chamber 55 is pumped through the tip 42 into the vessel 95. The moving of the piston 70 with respect to the pump chamber 55 results in a relative movement of the fluid reservoir 20 and the injector nozzle 40.

Figure 7:
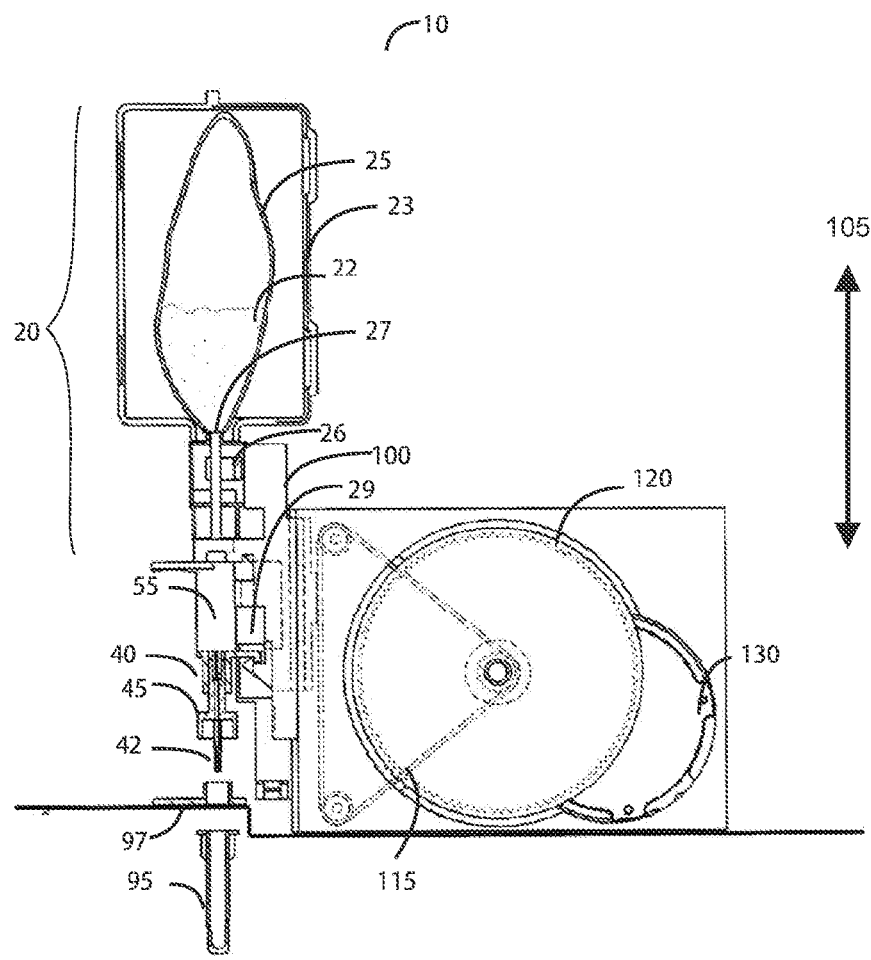
FIG. 7 shows the liquid handling device with an additional cover plate.

In a further aspect of the invention, as shown in FIG. 7, the actuator 97 is placed on a cover plate 98. In this case, the tip 42 passes through the bore of the actuator 97 and a further bore of the cover plate 98.

The injector nozzle 40, the fluid reservoir 20 and/or the pump chamber 55 can be completely disposed of and replaced after use, which avoids build up of debris on, for example, the tip 42

The carriage 100 may be mounted on a further device that moves the carriage in a plane or in a straight line so that a plurality of the vessel 95 can be filled.

Figure 8:
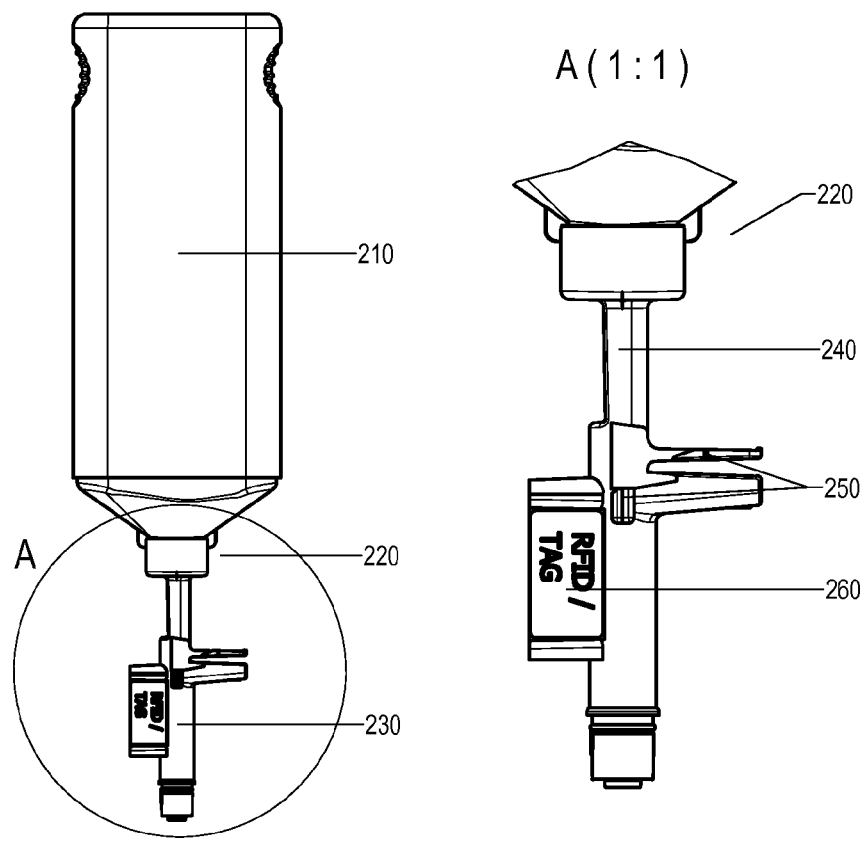
FIG. 8 shows a disposable dispenser unit comprising a bag in a bottle as the fluid reservoir and a measurement chamber.
Figure 13:
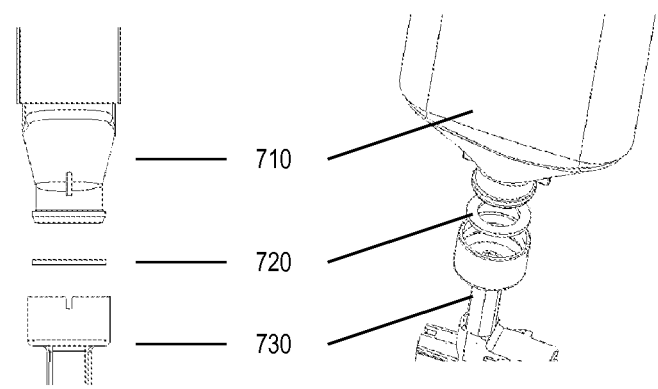
FIG. 13 shows a connection between a bottle as the fluid reservoir and the disposable dispenser cartridge.

FIG. 8 left shows one embodiment of a disposable dispenser unit comprising a bag in a bottle 210 as an airless fluid reservoir and a measurement chamber 240 for fluid detection. There is a snap-on connection 220 between the fluid reservoir (bag in a bottle 210) and the dispenser head 230. A close-up of one example of such a snap-on connection is shown in FIG. 13 (see below). The dispenser head 230 comprises a pump chamber comprising a piston and valves, and comprises an injector nozzle. On the right hand side, the bottom part of the disposable dispenser unit is shown more closely. The measurement chamber 240 is located between the snap-on connection 220 and attachment means 250. The attachment means 250 are fixtures at the dispenser head 230 to adapt the dispenser head 230 for example to an actuator within the diagnostic system. An RFID tag 260 is also attached to the dispenser head 230 for storing information.

Figure 9:
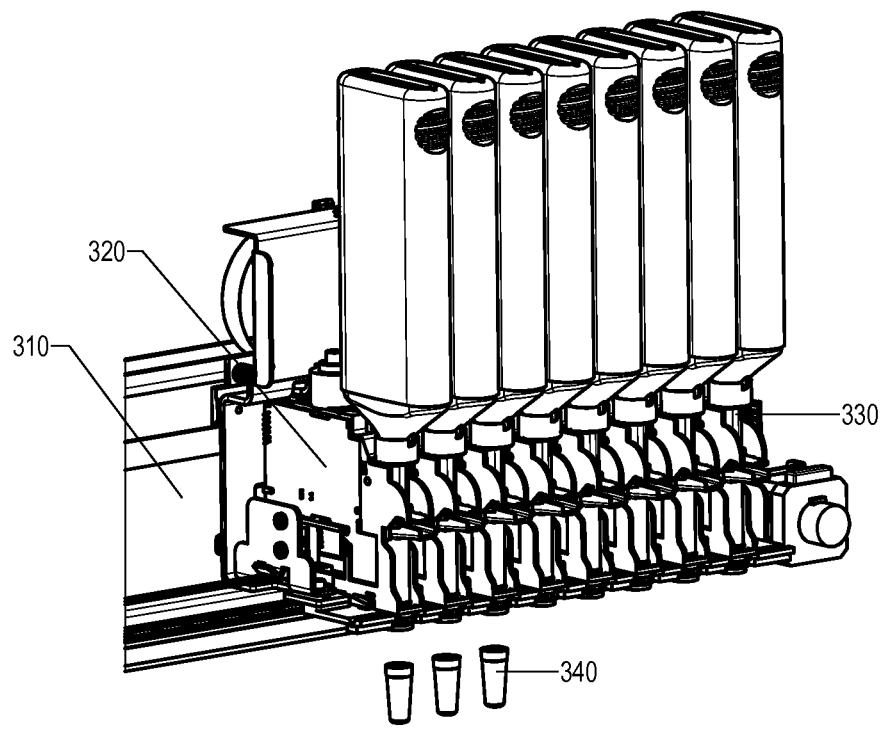
FIG. 9 shows a diagnostic system comprising a disposable dispenser cartridge actuator and a disposable dispenser cartridge.

FIG. 9 shows a mechanical interface 310 between several disposable dispenser cartridge actuators (DDCA) 320 and a diagnostic system. The diagnostic system also comprises several disposable dispenser cartridges (DDC) 330. The DDC 330 are loaded onto the DDCA 320 within the diagnostic system by the user. The DDC 330 and the DDCA 320 together allow the dispensing of the fluid contained in the fluid reservoir. The fluid is guided via the injector nozzle of the DDC 330 into any process cavity 340 in the diagnostic system.

Figure 10:
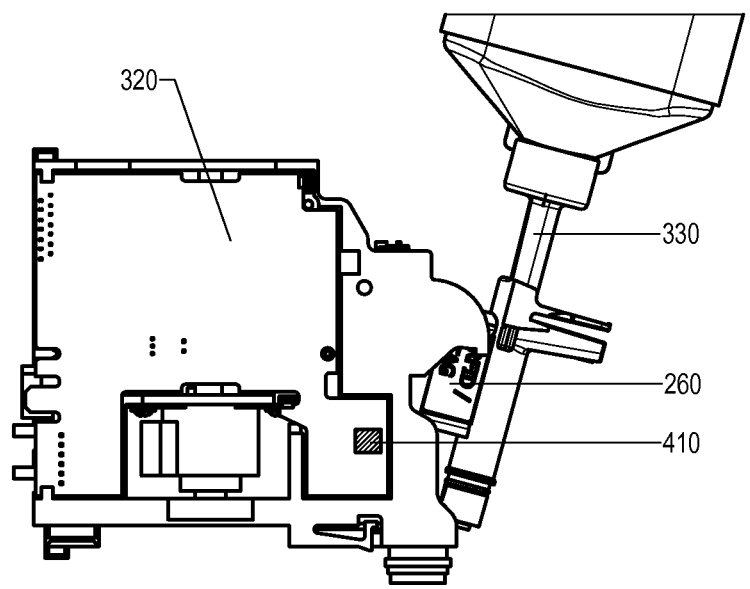
FIG. 10 shows a disposable dispenser cartridge actuator and a disposable dispenser cartridge comprising an RFID tag and an RFID reader.

FIG. 10 shows a disposable dispenser cartridge actuator 320 and a disposable dispenser cartridge 330 comprising an RFID tag 260 and an RFID reader 410. The fluid can be identified by the diagnostic system by means of an RFID tag 260 on the DDC 330 via an RFID reader 410 located at the DDCA 320 (integrated in the DDCA printed circuit board) because the information stored in the RFID tag 260 can be read by the RFID reader 410. The remaining fluid inventory can also be monitored. As shown in FIG. 10, the RFID reader 410 may be close to the DDC 330. It is also possible to use read-write RFID tags 260 which allow writing information on the RFID tag 260, for example consumption of fluid.

Figure 11:
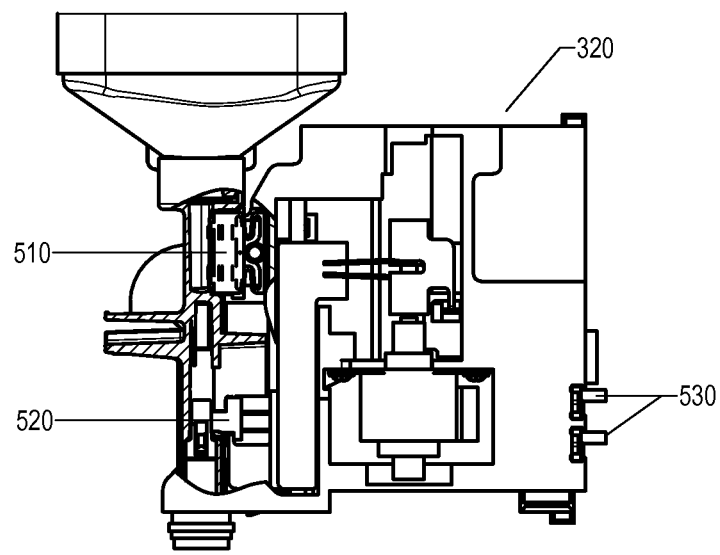
FIG. 11 shows a disposable dispenser cartridge actuator comprising a fluid detection sensor.
Figure 17:
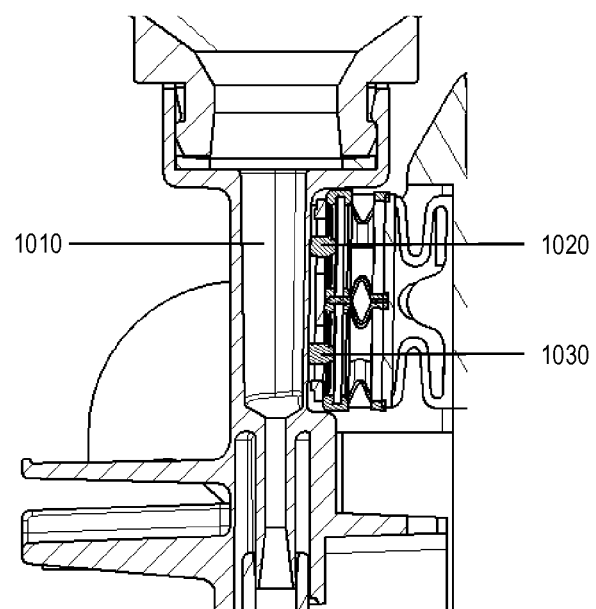
FIG. 17 shows a fluid detection sensor.

FIG. 11 shows a disposable dispenser cartridge actuator 320 comprising a fluid detection sensor 510 to avoid a further dispense when the DDC is empty (for further details regarding the fluid detection sensor, see FIG. 17). The DDCA 320 also comprises a spring-supported actuator 520 which ensures connection of the DDCA 320 to the piston of the DDC. The DDCA 320 further comprises coding pins 530 (for details see FIG. 23).

Figure 12:
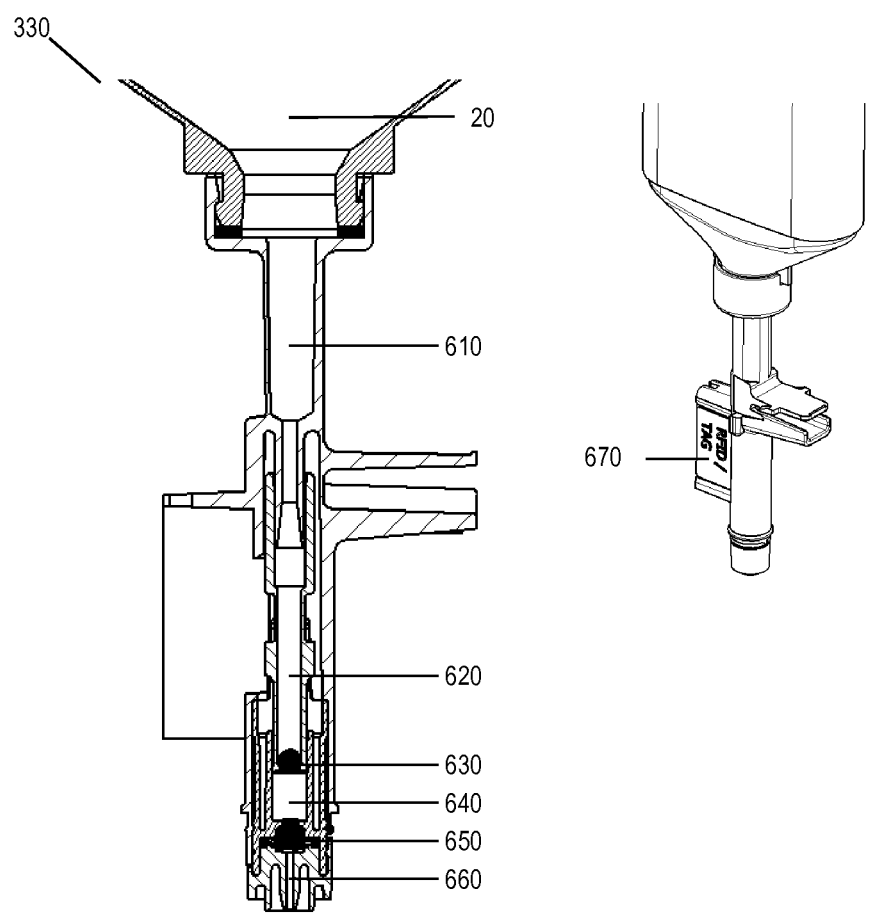
FIG. 12 represents one aspect of a disposable dispenser cartridge.

FIG. 12 represents one aspect of a disposable dispenser cartridge 330. The DDC 330 comprises a fluid reservoir 20, a measurement chamber 610, a piston 620 comprising an inlet valve 630, a pump chamber 640, an outlet valve 650, an injector nozzle 660 and an RFID tag 670. The DDC 330 of FIG. 12 works as a piston pump. By traveling up the piston 620, the pump chamber 640 will fill up from upside down. Thereby, the fluid streams through the inner of the piston 620 inside the pump chamber 640. Both valves (inlet valve 630 and outlet valve 650) are force loaded elastomere valves in this embodiment. When traveling piston 620 down, the fluid will pressed out through the injector nozzle 660. For applications with a medium to high requirement for precise dispense volumes, the piston 620 is working against hard stops within the pump chamber 640 (for details see FIG. 18). These pump principles allow to define the dispense volume/stroke by design within the pump chamber stops.

The outlet of the pump chamber 640 is directly connected to the injector nozzle 660, which is part of the dispenser head. The geometry, dimensions and orientation of the injector nozzle 660 can be adapted to the needs of the user within the diagnostic system.

It is also possible that the pump feeds several injector nozzles, so one pump can feed several connected injector nozzles for multi-dispensing.

FIG. 13 shows a connection between a bottle 710 as the fluid reservoir and the disposable dispenser cartridge. The bottle 710 is directly connected to the dispenser head 730 by an easy, one way, snap-on connection, after filling the bottle 710. A seal ring 720 is placed between the bottle 710 and the dispenser head 730 for tightening of the connection. There is no tubing between the bottle 710 and the dispenser head 730, so the dead volume is reduced.

Figure 14:
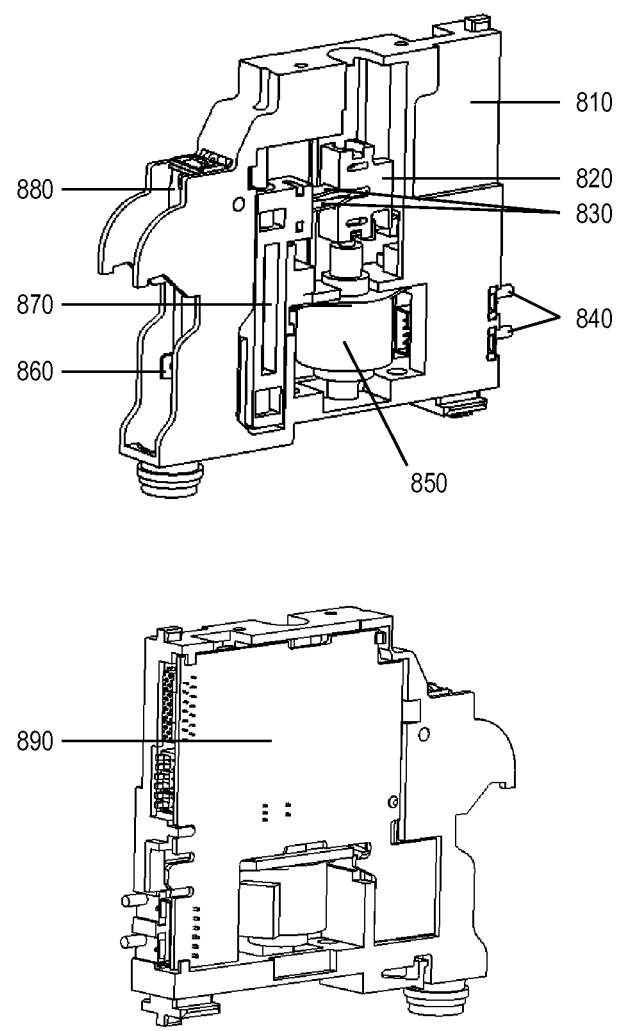
FIG. 14 represents one aspect of a disposable dispenser cartridge actuator.

FIG. 14 represents one aspect of a disposable dispenser cartridge actuator (DDCA). The DDCA comprises a housing 810, a motor lift 820, a spring 830, coding pins 840, a linear motor 850, an actuator 860, a lifting sledge 870, a fluid detection sensor 880 and a printed circuit board 890.

Figure 15:
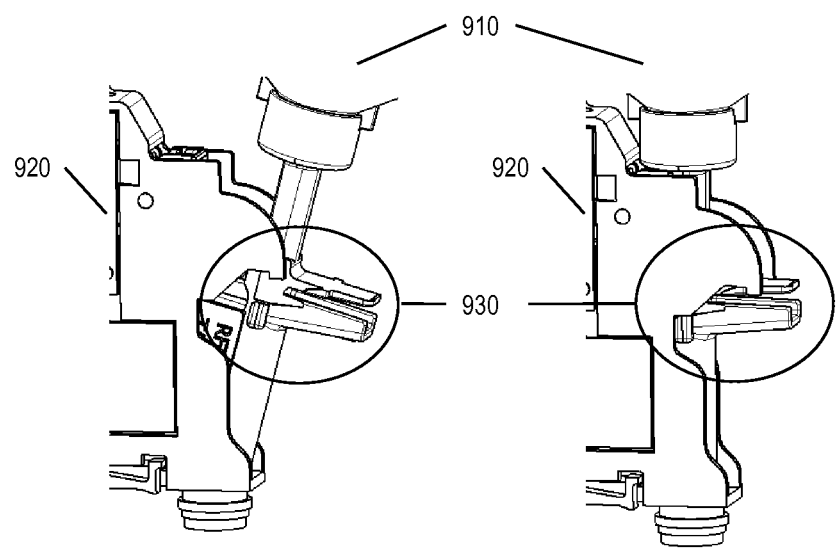
FIG. 15 shows an interface between a disposable dispenser cartridge and a disposable dispenser cartridge actuator.

FIG. 15 shows an interface between a disposable dispenser cartridge 910 and a disposable dispenser cartridge actuator 920. The DDC 910 will be loaded in a defined fixed position. Mechanical features on the DDC 910 and features on the DDCA 920 will ensure an easy loading/unloading by the user, for example by snap-on features 930. No tools are necessary and the loading and unloading process of the DDC 910 into the DDCA 920 will be easily accomplished in the correct position. There is no risk of misplacement. Such simple interfaces improve the handling of the disposable dispenser unit and the liquid handling device by the user (improvement of "men-machine" interface).

Figure 16:
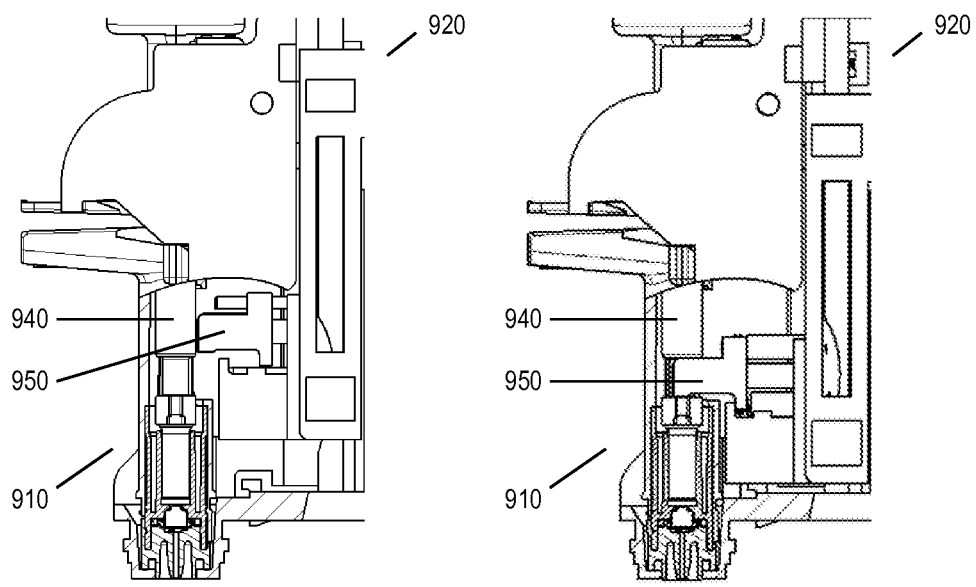
FIG. 16 shows a disposable dispenser cartridge connected to a disposable dispenser cartridge actuator before and after initial drive.

When the disposable dispenser cartridge 910 is loaded into the disposable dispenser cartridge actuator 920, the actuator 950 of the disposable dispenser cartridge actuator 920 is not necessarily in the correct position. FIG. 16 shows a disposable dispenser cartridge 910 connected to a disposable dispenser cartridge actuator 920 before (left, actuator not connected) and after (right, actuator connected) initial drive. The actuator 950 is spring-supported so that the loading of the DDC 910 is independent from the position of the actuator 950. After loading and initial drive of the DDCA 920 (FIG. 16 right), the actuator 950 will connect to the piston 940 of the DDC 910 and will operate with mechanical movements (up and down) the pump mechanism of the DDC 910.

FIG. 17 shows a fluid detection sensor. The fluid detection sensor connects to the very thin wall of the measurement chamber 1010 of the DDC. Thereby, a first pin 1020 gives a mechanical vibration, generated by a piezo membrane, to the wall of the measurement chamber 1010. In the same step, a second pin 1030 returns the vibration to a second piezo membrane. The measured signal differs in terms of amplitude and phase shift between stimulation and echo depending on if the measurement chamber 1010 is fluid-filled or air-filled. Therefore, an empty fluid reservoir can be detected.

In detail, the fluid detection process comprises the following steps:
- Inserting a new DDC with a filled measurement chamber
- Determining the stimulation frequency when the measured amplitude of the second piezo element reaches a maximum value which is the resonant frequency of the system with a filled measurement chamber
- Cyclic stimulation with resonant frequency and measurement of the echo (Signal of the second piezo element)
- Determining the amplitude and phase shift of the signal at resonant frequency by using FFT (noise filter)
- The stimulation can either be constant, or (in case of hearable frequencies) in small pulse packages of several, e.g. 10 periods at resonant frequency and an off time of several seconds in between to reduce noise.

Figure 18:
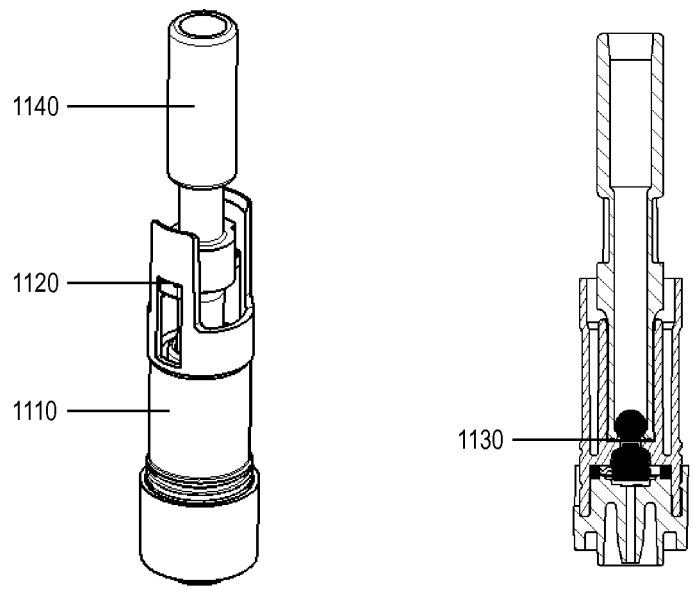
FIG. 18 shows a pump chamber comprising hard stops and a piston.

FIG. 18 shows a pump chamber 1110 comprising hard stops 1120 and 1130 and a piston 1140. Upper hard stop 1120 and lower hard stop 1130 ensure that precise volumes of fluid can be dispensed.

Figure 19:
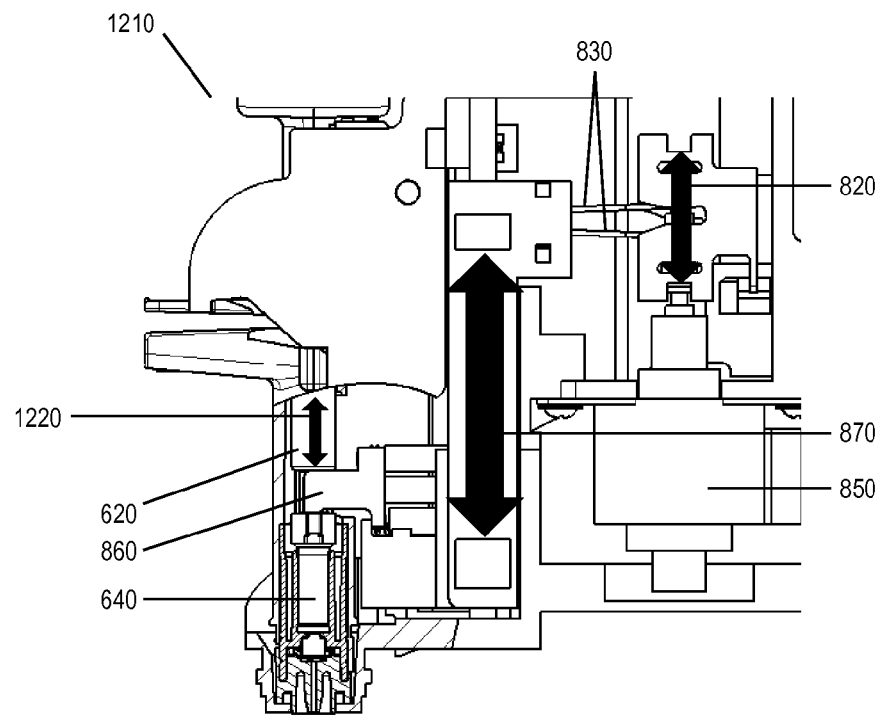
FIG. 19 shows the working process of a disposable dispenser cartridge actuator.

FIG. 19 shows the working process of a disposable dispenser cartridge actuator 1210. The DDCA 1210 activates the piston 620 inside the pump chamber 640 in z-direction 1220 up and down (shown by the arrows) in a defined way by the actuator 860. A full stroke of the actuator 860 allows a full/fixed volume to be dispensed. Thereby, the motor lift 820, directly mounted at the linear motor 850, moves the lifting sledge 870 up and down in z-direction. The connection between motor lift 820 and lifting sledge 870 works over two flat springs 830 which allow an over travel from the motor lift 820 against the lifting sledge 870. This will avoid that the hard piston stops inside the pump chamber 640 will damage the motor. The actuator 860 is simple and thus reduces complexity and system costs and improves reliability.

Figure 20:
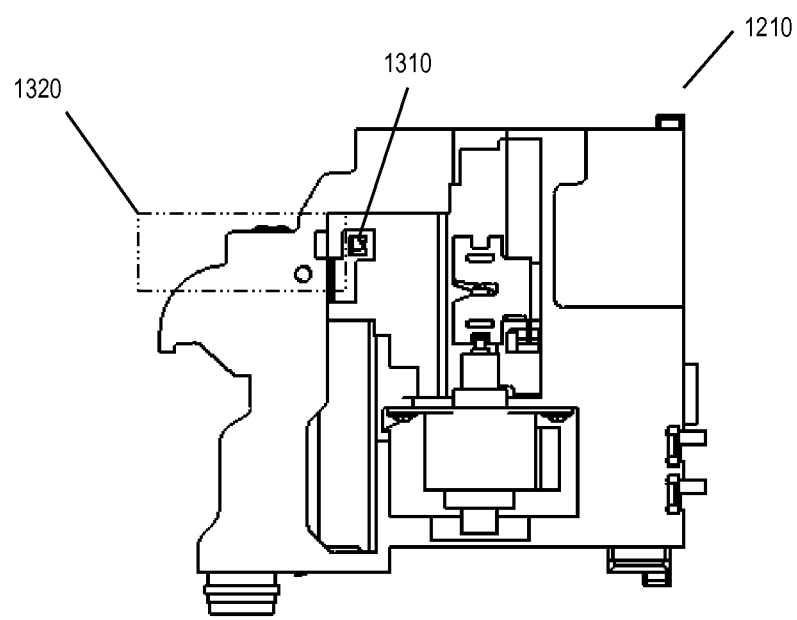
FIG. 20 shows an LED at the disposable dispenser cartridge actuator.

FIG. 20 shows an LED 1310 as well as light guide material 1320 at the disposable dispenser cartridge actuator 1210. The DDCA 1210 is able to indicate an empty fluid reservoir at the DDC or errors in the working process by the LED 1310.

Figure 21:
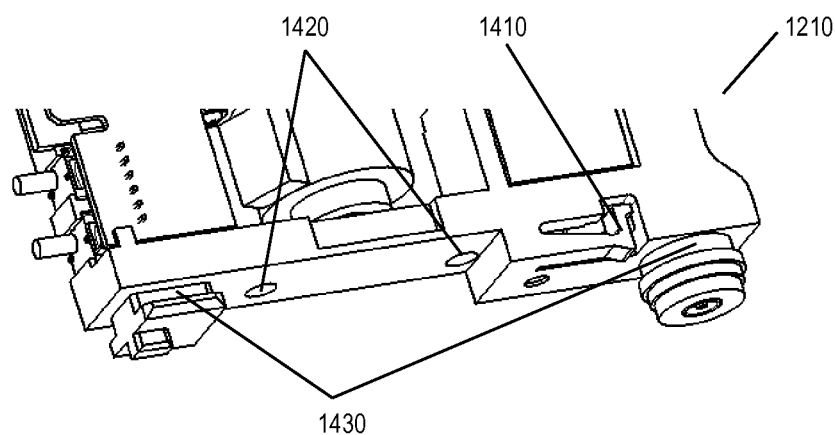
FIG. 21 shows an interface between a disposable dispenser cartridge actuator and a diagnostic system.

FIG. 21 shows an interface between a disposable dispenser cartridge actuator 1210 and a diagnostic system. The DDCA 1210 in FIG. 21 provides both a snap-on feature 1410 for fixation of the DDCA 1210 to a diagnostic system and the opportunity for fixation by screwing (screw positions 1420). Holding features 1430 for the snap-on function are also shown.

Figure 22:
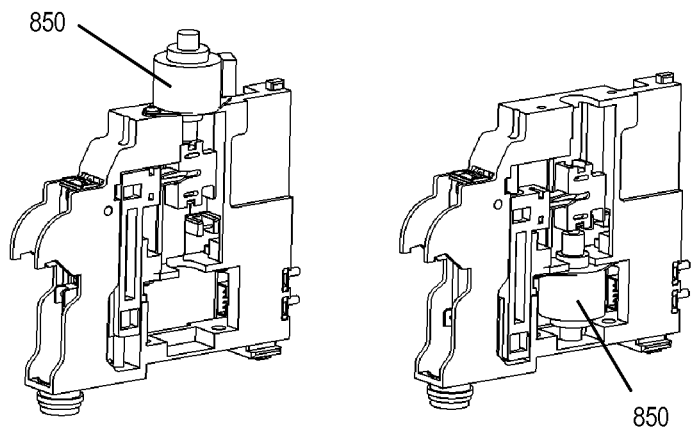
FIG. 22 shows a disposable dispenser cartridge actuator with a motor in an upper and in a lower position.

FIG. 22 shows a disposable dispenser cartridge actuator with a motor 850 in an upper (left) and in a lower position (right). This variability in the motor position allows the disposable dispenser cartridge actuator to be mounted in the same line in a grid of 18 mm.

Figure 23:
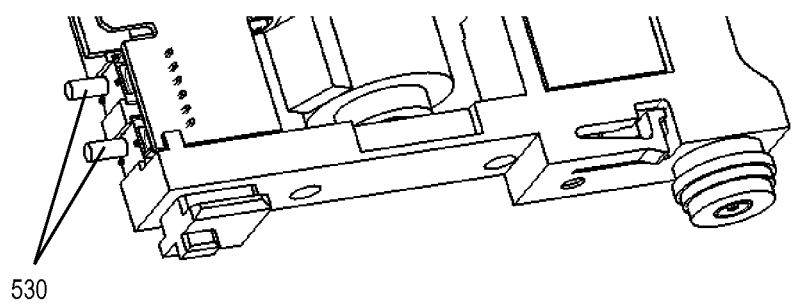
FIG. 23 shows coding pins at the disposable dispenser cartridge actuator.

FIG. 23 shows coding pins 530 at the disposable dispenser cartridge actuator. Thereby, a mechanical coding feature is included when the DDCA is connected to a diagnostic system.

REFERENCE NUMBER LIST

10 Liquid Handling Device
20 Fluid reservoir
21 Bottle
22 Fluid
23 Container
25 Bag
26 Fluid sensor
27 Opening
29 Identification tag
40 Injector Nozzle
42 Tip
45 Protective Cap/Abutment Part
55 Pump Chamber
62 Inlet valve
64 Outlet valve
70 Piston
72 Housing
95 Vessel
97 Actuator
98 Cover plate
100 Carriage
105 Double headed arrow
115 Belt
120 Cogwheel
130 Motor
210 bag in a bottle
220 snap-on connection
230 dispenser head
240 measurement chamber
250 attachment means
260 RFID tag
310 mechanical interface
320 disposable dispenser cartridge actuator (DDCA)
330 disposable dispenser cartridge (DDC)
340 process cavity
410 RFID reader
510 fluid detection sensor
520 spring-supported actuator
530 coding pins
610 measurement chamber
620 Piston
630 inlet valve
640 pump chamber
650 outlet valve
660 injector nozzle
670 RFID tag
710 Bottle
720 seal ring
730 dispenser head
810 Housing
820 motor lift
830 Spring
840 coding pins
850 linear motor
860 actuator
870 lifting sledge
880 fluid detection sensor
890 printed circuit board
910 disposable dispenser cartridge (DDC)
920 disposable dispenser cartridge actuator (DDCA)
930 snap-on feature
940 Piston
950 actuator
1010 measurement chamber
1020 first pin
1030 second pin
1110 pump chamber
1120 upper hard stop
1130 lower hard stop
1140 Piston
1210 disposable dispenser cartridge actuator (DDCA)
1220 piston in z-direction
1310 LED 1320 light guide material
1410 snap-on feature
1420 screw position
1430 holding features

What is claimed is:

1. A disposable dispenser unit comprising:
   a fluid reservoir,
   a measurement chamber for determining whether said fluid reservoir is fluid-filled,
   a tag for storing information,
   a dispenser head comprising:
      a pump chamber comprising a housing, an inlet valve and a piston arranged within the housing; and
      at least one injector nozzle fluidly connected to said pump chamber;
      wherein the dispenser head is fluidly connected to the fluid reservoir via said inlet valve of the pump chamber, wherein the piston comprises a volume which can be filled with fluid and an outlet valve; and
   wherein said tag is attached to one of said fluid reservoir and said dispenser head.

2. The disposable dispenser unit according to claim 1, wherein the tag is an RFID tag.

3. The disposable dispenser unit according to claim 1, further being made of an opaque material.

4. The disposable dispenser unit according to claim 1, further comprising a fluid sensor connected to said measurement chamber for detecting a fluid within the fluid reservoir.

5. The disposable dispenser unit according to claim 1, wherein the fluid reservoir is a bag or a bottle.

6. The disposable dispenser unit according to claim 5, wherein the bag is flexible.

7. The disposable dispenser unit according to claim 1, wherein said fluid reservoir comprises a container and a bag located within said container.

8. The disposable dispenser unit according to claim 1, wherein the fluid reservoir is located above the pump chamber.

9. The disposable dispenser unit according to claim 1, wherein the fluid reservoir is directly connected to the pump chamber, and/or the pump chamber is directly connected to the at least one injector nozzle.

10. A liquid handling device comprising
    a disposable dispenser unit comprising:
    a fluid reservoir,
    a measurement chamber for determining whether said fluid reservoir is fluid-filled,
    a tag for storing information,
    a dispenser head comprising:
       a pump chamber comprising:
          a housing;
          an inlet valve; and
          a piston arranged within the housing, the piston comprising a volume that can be filled with a fluid and an outlet valve; and
       an injector nozzle fluidly connected to said pump chamber, and
    an actuator for actuating the disposable dispenser unit;
    wherein the dispenser head is fluidly connected to the fluid reservoir via the inlet valve of the pump chamber.

11. The liquid handling device of claim 10, wherein the disposable dispenser actuator comprises a fluid detection sensor.

* * * * *